(12) United States Patent
Park et al.

(10) Patent No.: US 7,638,274 B2
(45) Date of Patent: Dec. 29, 2009

(54) POLYNUCLEOTIDE ASSOCIATED WITH A COLON CANCER COMPRISING SINGLE NUCLEOTIDE POLYMORPHISM, MICROARRAY AND DIAGNOSTIC KIT COMPRISING THE SAME AND METHOD FOR DIAGNOSING A COLON CANCER USING THE POLYNUCLEOTIDE

(75) Inventors: Kyung-Hee Park, Seoul (KR); Kyu-Sang Lee, Suwon-si (KR); Yeon-Su Lee, Goyang-si (KR); Jae-Heup Kim, Seoul (KR); Yeon-A Park, Yongin-si (KR); Ji-Young Cho, Daejeon-si (KR); Ok-Kyoung Son, Seoul (KR); Byung-Chul Kim, Hwaseong-si (KR); Min-Sun Kim, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 420 days.

(21) Appl. No.: 10/549,661

(22) PCT Filed: Feb. 19, 2005

(86) PCT No.: PCT/KR2005/000465

§ 371 (c)(1),
(2), (4) Date: Sep. 16, 2005

(87) PCT Pub. No.: WO2005/079173

PCT Pub. Date: Sep. 1, 2005

(65) Prior Publication Data

US 2007/0128602 A1 Jun. 7, 2007

(30) Foreign Application Priority Data

Feb. 20, 2004 (KR) ...................... 10-2004-0011327
Feb. 18, 2005 (KR) ...................... 10-2005-0013395

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search ................ None
See application file for complete search history.

(56) References Cited

U.S. PATENT DOCUMENTS

2005/0228172 A9 * 10/2005 Wang .................... 536/24.3

FOREIGN PATENT DOCUMENTS

JP 2003235576 8/2003

OTHER PUBLICATIONS

Genbank GenBank Reference SNP rs11408214m, entry date Nov. 13, 2003 URL: http://www.ncbi.nlm.nih.gov/SNP/snp_ref. cgi?db=human_9606&na=1&gnl=gnl%7CdbSNP%7Crs11408214 &RID=KVW71K0401R&QUERY_NUMBER=1.*
Hirschhorn et al. Genetics in Medicine. vol. 4, No. 2, pp. 45-61, Mar. 2002.*
Long, et al. BMC Genet. May 24, 2004;5:11.*
Halushka, et al. Nature Genetics, 1999; 22:239-247.*
DNA Polymorphism and Human Disease; J.F. Gusella; Ann. Rev. Biochem. 1986. 55:831-52.
Sequence-Selective Recognition of DNA by Strand Displacement with a Thymine-Substituted Polyamide; Peter E. Nielsen, Michael Egholm, Rolf H. Berg, Ole Buchardt; Science, vol. 254; Dec. 6, 1991; pp. 1497-1500.
The Ligation Amplification Reaction (LAR)-Amplification of Specific DNA Sequences Using Sequential Rounds of Template-Dependent Ligation; Dan Y. Wu, R. Bruce Wallace; Genomics 4, 560-569 (1989).
A Ligase-Mediated Gene Detection Technique; Ulf Landegren, Robert Kaiser, Jane Sanders, Leroy Hood; Aug. 26, 1988; Division of Biology, California Institute of Technology, Pasadena, CA 91125.
Transcription-based amplification system and detection of amplified human immunodeficiency virus type 1 with a bead-based sandwich hybridization format; D.Y. Kwoh, G.R. Davis, K.M. Whitfield, H.L. Chappelle, L.J. DiMichele, T.R. Gingeras; Proc. Natl. Acad. Sci USA, vol. 86, pp. 1173-1177, Feb. 1989.
Isothermal, in vitro amplification of nucleic acids by a multienzyme reaction modeled after retroviral replication; John C.Guatelli, Kristina M. Whitfield, Deborah Y. Kwoh, Kevin J. Barringer, Douglas D. Richman, Thomas R. Gingeras; Proc. Natl. Acad. Sci USA; vol. 87, pp. 1874-1878, Mar. 1990, Biochemistry.
Molecular Cloning; A Laboratory Manual; Second Edition; Sambrook, Fritsch, Maniatis, pp. 13.1-13.20.
"DNA Polymorphism and Human Diease"; Author: J.F. Gusella; Annu. Rev. Biochem,. vol. 55, pp. 831-854 (1986).
PCT International Search Report; International Application No. PCT/KR2005/000465; International filing date Feb. 19, 2005; Date of mailing: Jun. 29, 2005.
PCT Written Opinion for International Application No. PCT/KR2005/000465; International filing date Feb. 19, 2005; Date of Mailing: Jun. 29, 2005.
Haga, Hisanori et al., "Gene-based SNP discovery as part of the Japanese Millennium Genome Project: identification of 190562 genetic variations in the human genome," JHum Genet (2002) 47: 605-610.
Kawakami, Kazuyuki and Watanabe, Go, "Identification and Functional Analysis of Single Nucleotide Polymorphism in the Tandem Repeat Sequence of Thymidylate Synthase Gene," Cancer Research (2003) 63: 6004-6007.

(Continued)

*Primary Examiner*—Jeanine A Goldberg
(74) *Attorney, Agent, or Firm*—Cantor Colburn LLP

(57) ABSTRACT

Provided is a polynucleotide including at least 10 contiguous nucleotides of a nucleotide sequence selected from the group consisting of nucleotide sequences of SEQ ID NOS: 1-12 and including a nucleotide at position 101 of the nucleotide sequence, or a complementary polynucleotide thereof.

3 Claims, No Drawings

OTHER PUBLICATIONS

Powell, Ned et al., "Single nucleotide polymorphism analysis in the human phosphatase PTPrj gene using matrix-assisted laser desorption/ionisation time-of-flight mass spectrometry," Rapid Commun. Mass Spectrom/ (2004) 18: 2249-2254.
NCBI Single Nucleotide Polymorphism, Reference SNP Id: rs2295706, NCBI Assay Id: ss12673809 (Aug. 27, 2003).
Molecular Cloning; A Laboratory Manual; Second Edition; Sambrook, Fritsch, Maniatis, 1989.
XP002529404 retrieved from NCBI database accession no. rs2863383; (Oct. 10, 2003).
XP002529409 retrieved from NCBI database accession no. rs1485217; (Oct. 10, 2003).
XP002529410 retrieved from NCBI database accession no. rs1996489; (Nov. 22, 2003).
XP002529415 retrieved from NCBI database submitter method handle TSC-CSHL, (May 25, 2006).
International Search Report for PCT/KR2005000465.
XP002529405 retrieved from NCBI database accession no. rs7151139; (Jun. 30, 2003).
XP002529406 retrieved from NCBI database accession no. rs724454; (Jun. 9, 2000).
XP002529407 retrieved from NCBI database accession no. rs10142383; (Apr. 11, 2003).
XP002529408 retrieved from NCBI database accession no. rs1402026; (May 11, 2003).
XP002529411 retrieved from NCBI database accession no. rs2236261; (Oct. 10, 2003).
XP002529418 retrieved from NCBI database submitter method handle Perlegen, (May 25, 2006).
XP002529416 retrieved from NCBI database submitter method handle BCM_SSAHASNP, May 25, 2006).
XP002529417 retrieved from NCBI database submitter method handle WI_SSAHASNP, (May 25, 2006).
XP002529412 retrieved from NCBI database accession no. rs1340655; (Oct. 10, 2003).
XP002529413 retrieved from NCBI database accession no. rs1334856; (Oct. 19, 2000).
XP002529414 retrieved from NCBI database accession no. rs6573195; (Oct. 10, 2003).
Erichsen et al., "SNPs in cancer research and treatment," British Journal of Cancer, vol. 90, No. 4, pp. 747-751, (Feb. 17, 2004).
Sihn et al., "CANu1, a novel nucleolar protein, accumulated on centromere in response to DNA damage," Genes to Cells, vol. 13, No. 8, pp. 787-796, (Aug. 2008).
Twymann et al., "Techniques Patents for SNP Genotyping," Pharmacogenomics, vol. 4, No. 1, pp. 67-69, (Jan. 01, 2003).

* cited by examiner

SEQUENCE LISTING

```
<160> NUMBER OF SEQ ID NOS: 48

<210> SEQ ID NO 1
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or C, polymorphic site

<400> SEQUENCE: 1
tacattactg tattgtatac attttgtcta tttcttcttt gattttgttt ttgtttttat      60
aattatttca ggtgtgggga aaaattctgt ccctgatact ncatcttgtc cagaactgga     120
agagctcatt atttctttat ttgtactgtt tttatctatt catccatagt gttctcaaca     180
gagctatcaa aagtattatc a                                               201

<210> SEQ ID NO 2
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 2
tctataccac agtagtgttg atctcaagag cttagcatgt tggcttaaag acatccaggg      60
atgaggtgtt ggagtcagat tgagtttgaa tcttagctct ncttgtatta ctgtgttatc     120
ttggccaagt atttaacctc tctgaaatag gttttctcag ggctgtgaag tttggaagat     180
acataaaagc ccaaagaaaa a                                               201
```

<210> SEQ ID NO 3
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or C, polymorphic site

<400> SEQUENCE: 3
ccttaaggtg dacagaaaat gaattgtttc cttcttacca tctgttattg tttttgcctg      60
aaggcctgac tgccttccta ctccctaata aacaaagggg nattctattg accaattcat    120
tttcaaagag atttttaaaag gcattaagca atcaattctc acatagtgtc caaattgagt    180
ctctcattca ttctcttgcc t                                              201

<210> SEQ ID NO 4
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=G or C, polymorphic site

<400> SEQUENCE: 4
tgacctcagg tgatccaccc acctcggcat cccaaagtgc tgggattaca ggtgtgagcc      60
accacaccag gccttgggta ccatgccttg aaccatttca ntgccttttg gagatggatg    120
agttgccagc atccttctta gatccctata tatttgttta tttattgaac aaatacatat    180
taacttatct ttttgaccaa a                                              201

<210> SEQ ID NO 5
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=G or T, polymorphic site

<400> SEQUENCE: 5
cccaggattg gaaatgatgg atgctttcca ggggccccga tccatcatca gatgaatacg      60
cagccccctc cccaaggaag ctcctggttc attgagatgc ntaattctct ccttatttc     120 attactgttt ctcgtttgta tggattattt ttcttcagta atctgggctt tacatgactg    180
aataagaaaa tcatttgttc a                                              201

<210> SEQ ID NO 6
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or T, polymorphic site

<400> SEQUENCE: 6
atttcctgcc tgtgataaat gtgtcccaat atttgtcttt tggttgttgt tgttgagaat      60
catttctcat gttgggaaat gtgaagtcaa atagtgtgac nggacttgct gaatgattga    120
gtcaaccaca aatggtattg tcaaccatgg ctgttgaatt aatgagaaca attaaaactc    180 attttttcaga ggtcaaaaga t                                             201

<210> SEQ ID NO 7
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=G or T, polymorphic site

<400> SEQUENCE: 7

```
attagctaaa cagtttaatg atgatctgcc aagaaattga tgtcagcagt tagaaaacta      60
aagtcctttt ttatgcagag acagcacagt tggtaaaatt nttatagttg acaagttgga     120
aagcagtgca tgtctctgac aagacttcag ctctgtggga agtgtttgga aagaaatgga    180
gtgatagtgt ttgttggcat t                                               201
```

<210> SEQ ID NO 8
<211> LENGTH: 201
<212> TYPE: DNA
<213> ORGANISM: Homo sapiens
<220> FEATURE:
<221> NAME/KEY: variation
<222> LOCATION: (45)
<223> OTHER INFORMATION: n=A, T, G or C

<400> SEQUENCE: 8

```
tgctcatgta ccttatggat ttgacccacc tcattctgga caaancctca ggaggatctc      60
ttcagggaca tgatgcagtt tgagactgg tggagattcg macggtatga agcatttggc     120
ttcttggagt tttaggtttc taaattttga gctccaaggg tatcacacag tagctctcat     180
ttaagtgagt cttctcatgt t                                               201
```

<210> SEQ ID NO 9
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=G or T, polymorphic site

<400> SEQUENCE: 9

```
aatatgatgt cttggatttg cttcaaaata atacaagaaa agggtttgac ttttggtcag      60
tatatagatg agtcatgact gaccatgggg tgacaattgt ngaagctgag ttaggtaccc    120
agaggttcgt tataatattc tgtctatgtt aatctgcaat atgtctgaca ttttttataa    180
ttaaaacttc ttttgaaaag a                                               201
```

<210> SEQ ID NO 10
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=G or T, polymorphic site

<400> SEQUENCE: 10

```
attaaaaaac ctgtattttt ggatgtattt ttagaaaaac agatttacag gaaacaaacc      60
aaacaaaaag acttgtggta caagaaaatt agaaaataca ntatatttaa aatggacgtg    120
ttagcttgtc ccaggtaaac tcagttcaaa atatgggata aaagagattt tactttaac     180
```

```
ttcgaacagc tagagaatga t                                              201

<210> SEQ ID NO 11
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 11
aattggtaat tactttgatt aaattaattt aaaacttggc agtctgtgga gacattttg      60 attgttagag cttggagggg ccatccgtgg gaagaggcca nggatgctgc tggaaaccta   120
caatgcccag gacagccctc aacaaaaaat gttctggctt caaatgtcaa tagctctgag   180
attgagaaac cctgttatag t                                              201

<210> SEQ ID NO 12
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 12
aagcagaaga tgaccagtct gaggcttcag ggaagaaatc tgtgaaggga gtgtctaaga     60
aatatgttcc tccacgcttg gttccagtac attatggtat naactttggc tgctgcctcc   120
tcagcatgaa ctgtttctct tttctctgtt cttggataac cctgcttatt ttcatcatgt   180
agatgaaaca gaagctgagc g                                              201

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
acgttggatg gagctcttcc agttctggac                                      30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
acgttggatg tcaggtgtgg ggaaaaattc                                      30

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
tccagttctg gacaagatg                                                  19
```

```
<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
acgttggatg aaagacatcc agggatgagg                                        30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
acgttggatg acttggccaa gataacacag                                        30

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgagtttgaa tcttagctct                                                   20

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
acgttggatg tggacactat gtgagaattg                                        30

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
acgttggatg ccttcctact ccctaataaa c                                      31

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
tgaaaatgaa ttggtcaata gaat                                              24

<210> SEQ ID NO 22
<211> LENGTH: 30
<212> TYPE: DNA
<213> ORGANISM: Artificial Sequence
<220> FEATURE:
<223> OTHER INFORMATION: primer
```

```
<400> SEQUENCE: 22
acgttggatg gggatctaag aaggatgctg                                  30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
acgttggatg ttgggtacca tgccttgaac                                  30

<210> SEQ ID NO 24
<211> LENGTH: 17
<212> TYPE: DNA
<213> ORGANISM: Artificial Sequence
<220> FEATURE:
<223> OTHER INFORMATION: primer

<400> SEQUENCE: 24
tccatctcca aaaggca                                                17

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
acgttggatg aaggaagctc ctggttcatt                                  30

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
acgttggatg tccatacaaa cgagaaacag                                  30

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ctcctggttc attgagatgc                                             20

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
acgttggatg ggttgactca atcattcagc                                  30

<210> SEQ ID NO 29
<211> LENGTH: 31
```

<212> TYPE: DNA
<213> ORGANISM: Artificial Sequence
<220> FEATURE:
<223> OTHER INFORMATION: primer

<400> SEQUENCE: 29
acgttggatg ctcatgttgg gaaatgtgaa g                                  31

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
actcaatcat tcagcaagtc c                                             21

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
acgttggatg atgcagagac agcacagttg                                    30

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
acgttggatg gtcttgtcag agacatgcac                                    30

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
agacagcaca gttggtaaaa tt                                            22

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
acgttggatg actgtgtgat acccttggag                                    30

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
acgttggatg tgcagttttg agactggtgg                          30

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
gccaaatgct tcataccgt                                      19

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
acgttggatg ataacgaacc tctgggtacc                          30

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
acgttggatg tgagtcatga ctgaccatgg                          30

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
tgggtaccta actcagcttc                                     20

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
acgttggatg tttacctggg acaagctaac                          30

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
acgttggatg ccaaacaaaa agacttgtgg                          30

<210> SEQ ID NO 42
<211> LENGTH: 24
<212> TYPE: DNA
<213> ORGANISM: Artificial Sequence -continued

```
<220> FEATURE:
<223> OTHER INFORMATION: primer

<400> SEQUENCE: 42
gctaacacgt ccattttaaa tata                                         24

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
acgttggatg tcctgggcat tgtaggtttc                                   30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
acgttggatg gattgttaga gcttggaggg                                   30

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gtaggtttcc agcagcatcc                                              20

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
acgttggatg agaaatatgt tcctccacgc                                   30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
acgttggatg aacagttcat gctgaggagg                                   30

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
ggttccagta cattatggta t                                            21
```

POLYNUCLEOTIDE ASSOCIATED WITH A COLON CANCER COMPRISING SINGLE NUCLEOTIDE POLYMORPHISM, MICROARRAY AND DIAGNOSTIC KIT COMPRISING THE SAME AND METHOD FOR DIAGNOSING A COLON CANCER USING THE POLYNUCLEOTIDE

CROSS-REFERENCE TO RELATED APPLICATIONS

This application is a 371 national stage of PCT/KR2005/000465 filed on Feb. 19, 2005, which claims the benefit of the filing date of Korean Patent Application No. 10-2004-0011327, filed on Feb. 2, 2004 and Korean Patent Application No. 10-2005-0013395, filed on Feb. 18, 2005, in the Korean Intellectual Property Office.

FIELD OF THE INVENTION

The present invention relates to a polynucleotide associated with colorectal cancer, a microarray and a diagnostic kit including the same, and a method of analyzing polynucleotides associated with colorectal cancer.

DESCRIPTION OF THE RELATED ART

The genomes of all organisms undergo spontaneous mutation in the course of their continuing evolution, generating variant forms of progenitor nucleic acid sequences (Gusella, Ann. Rev. Biochem. 55, 831-854 (1986)). The variant forms may confer an evolutionary advantage or disadvantage, relative to a progenitor form, or may be neutral. In some instances, a variant form confers a lethal disadvantage and is not transmitted to subsequent generations of the organism. In other instances, a variant form confers an evolutionary advantage to the species and is eventually permanently incorporated into the DNA of most members of the species and effectively becomes the progenitor form. In many instances, both progenitor and variant form(s) survive and co-exist in a population of species. The coexistence of multiple forms of a sequence gives rise to polymorphisms.

Among polymorphisms, several types have been known, including restriction fragment length polymorphisms (RFLPs), short tandem repeats (STRs), variable number tandem repeats (VNTRs) and single-nucleotide polymorphisms (SNPs). Among them, SNPs take the form of single-nucleotide variations between individuals of the same species. When SNPs occur in protein coding sequences, some of the polymorphic forms may give rise to the non-synonymous change of amino acid causing expression of a defective or a variant protein. On the other hand, when SNPs occur in non-coding sequences, e.g., within intron, some of these polymorphisms may result in splicing variant of mRNA causing the expression of defective or variant proteins, too. Other SNPs could have no phenotypic effect at all.

It is estimated that human SNPs occur at a frequency of 1 in every 1,000 bp. When such SNPs influence the phenotypic expression such as a disease, polynucleotides containing the SNPs can be used as primers or probes for diagnosis of the disease. Monoclonal antibodies specifically binding with the SNPs can also be used in diagnosis of the disease. Currently, research into the nucleotide sequences and functions of SNPs is under way by many research institutes. The nucleotide sequences and other experimental results of the identified human SNPs have been made into database to be easily accessible.

Even though findings available to date show that specific SNPs exist on human genomes or cDNAs, phenotypic effects of SNPs have not been revealed. Functions of most SNPs have not been disclosed yet except a small numbers of SNPs.

Colorectal cancer is a cancer that is very common in worldwide including Korea. In Korea, colorectal cancer is the fourth common cancer in both men and women. Colorectal cancer ranks fourth among cause of death by cancer and is responsible for about seven deaths per hundred thousand populations. Over the last 10 years, the death rate for colorectal cancer is increasing by about 80%.

It is known that the incidence of colorectal cancer is mainly caused by an environmental factor. Rapid westernization of diet and excess intake of animal fat or protein are major factors in the development of colorectal cancer. However, it is known that about 5% of colorectal cancer cases occur by a genetic cause.

More than 90% of colorectal cancer patients are those who are over 40 years of age. It is known that the incidence of colorectal cancer is more frequent in people (high risk group) with familial history related to colorectal cancer, inflammatory bowel disease, colonic polyp, ovarian cancer, uterine cancer, and breast cancer, in addition to people aged over 40 years. The incidence of colorectal cancer in young people with 30-40 ages is mainly dominated by a genetic cause.

Early detection of colorectal cancer ensures almost 100% cure rate. Generally, however, since colorectal cancer has no specific early symptoms, early detection is difficult. A fecal occult blood test (for detecting trace amounts of blood in the stool) is generally used as a screening test to detect colorectal cancer, in particular when the cancer is not causing any symptoms. The fecal occult blood test is a method for selecting persons for an additional precision examination. However, since this test has a high rate of false-positive results and false-negative results, it is not suitable for early diagnosis. Currently, exact diagnosis of colorectal cancer is made by barium enema examination, endoscopy, radiation examination, and the like. A tumor marker called as CEA (carcinoembryonic antigen) is generally used to determine a developmental stage of colorectal cancer and to evaluate a therapeutic effect for colorectal cancer. But, still there are no universally recognized and verified tumor markers that enable early diagnosis or prediction of colorectal cancer through blood test. Several markers for screening or early diagnosis of patients belonging to high-risk groups who are susceptible to colorectal cancer are reported, but these markers have a limitation to be applied for most patients suffering colorectal cancer.

The most serious problem in early diagnosis or prognosis of various cancers and complicated diseases, including colorectal cancer, is that the diagnosis or prediction could be performed by a physical technique when the cancers and complicated diseases are at an advanced stage. However, the developments of recent various molecular biological techniques and the preliminary completion of the human genome project enable finding of genes or genetic variations directly/indirectly related to a disease. Therefore, early diagnosis that predicts the incidence of a disease using a genetic factor, instead of using a conventional phenotype- or phenotypic disease-dependent diagnostic method, becomes available. Currently, biochemical or molecular biological techniques are available for colorectal cancer diagnosis. Due to the lack of information about genes or genetic variations related to the cancer and correlation between the genes or genetic variations and colorectal cancer incidence rate, early diagnosis of a desired level for both patients and doctors is not made in case of colorectal cancer diagnosis using molecular biological techniques. Additionally, in most diagnosis cases using a single biological marker, it is common that the sensitivity and specificity of the marker are not satisfied at the same time. Generally, if sensitivity is high, specificity is low, and vice versa. For this reason, the possibility to occur error in diagnosis is high so that it is difficult to accomplish accuracy of a desired level. Therefore, a single biological marker is used simply as diagnostic markers of preliminary screening for precise examinations.

SUMMARY OF THE INVENTION

The present invention provides a polynucleotide containing single-nucleotide polymorphism associated with colorectal cancer.

The present invention also provides a microarray and a colorectal cancer diagnostic kit, each of which includes the polynucleotide containing single-nucleotide polymorphism associated with colorectal cancer.

The present invention also provides a method of diagnosing a colorectal cancer using polynucleotides associated with colorectal cancer.

DETAILED DESCRIPTION OF THE INVENTION

The present invention provides a polynucleotide including at least 10 contiguous nucleotides of a nucleotide sequence selected from the group consisting of nucleotide sequences of SEQ ID NOS: 1-12 and including a nucleotide of a polymorphic site (position 101) of the nucleotide sequence, or a complementary polynucleotide thereof.

The polynucleotide includes at least 10 contiguous nucleotides containing the nucleotide (expressed by "n") of a polymorphic site (position 101) of a nucleotide sequence selected from the nucleotide sequences of SEQ ID NOS: 1-12. The polynucleotide preferably is 10 to 200 nucleotides in length, more preferably 10 to 100 nucleotides in length, and still more preferably 10 to 50 nucleotides in length.

Each of the nucleotide sequences of SEQ ID NOS: 1-12 is a polymorphic sequence. The polymorphic sequence refers to a nucleotide sequence containing a polymorphic site at which single-nucleotide polymorphism (SNP) occurs. The polymorphic site refers to a position of the polymorphic sequence at which SNP occurs. The nucleotide sequences may be DNAs or RNAs.

In the present invention, each polymorphic site (position 101) of the polymorphic sequences of SEQ ID NOS: 1-12 is associated with colorectal cancer. This is confirmed by DNA nucleotide sequence analysis of blood samples from colorectal cancer patients and normal persons. The analysis results are summarized in Tables 1 and 2.

TABLE 1

Association of the polymorphic sequences of SEQ ID NOS: 1-12 with colorectal cancer

| ASSAY_ID | SNP | SNP sequence (SEQ ID NO.) | Allele frequency cas_A2 | Allele frequency con_A2 | Delta | Genotype frequency cas_A1A1 | cas_A1A2 | cas_A2A2 | con_A1A1 | con_A1A2 | con_A2A2 |
|---|---|---|---|---|---|---|---|---|---|---|---|
| CCK048 | [A/C] | 1 | 0.945 | 0.973 | 0.028 | 0 | 25 | 204 | 0 | 16 | 277 |
| CCK061 | [A/G] | 2 | 0.646 | 0.714 | 0.068 | 31 | 101 | 98 | 22 | 120 | 145 |
| CCK117 | [A/C] | 3 | 0.636 | 0.555 | 0.081 | 24 | 107 | 82 | 51 | 157 | 83 |
| CCK162 | [G/C] | 4 | 0.647 | 0.714 | 0.067 | 31 | 99 | 98 | 21 | 120 | 142 |
| CCY_041 | [T/G] | 5 | 0.61 | 0.507 | 0.103 | 32 | 109 | 81 | 67 | 140 | 71 |
| CCY_056 | [A/T] | 6 | 0.39 | 0.299 | 0.091 | 106 | 60 | 57 | 144 | 120 | 27 |
| CCY_065 | [T/G] | 7 | 0.409 | 0.328 | 0.081 | 84 | 105 | 42 | 132 | 126 | 32 |
| CCY_067 | [A/C] | 8 | 0.377 | 0.286 | 0.091 | 97 | 85 | 42 | 147 | 123 | 22 |
| CCY_071 | [G/T] | 9 | 0.754 | 0.821 | 0.067 | 34 | 45 | 151 | 13 | 77 | 197 |
| CCY_093 | [G/T] | 10 | 0.413 | 0.478 | 0.065 | 74 | 121 | 34 | 81 | 140 | 68 |
| CCY_202 | [G/A] | 11 | 0.355 | 0.285 | 0.07 | 103 | 106 | 33 | 148 | 123 | 22 |
| CCY_205 | [A/G] | 12 | 0.631 | 0.704 | 0.073 | 33 | 108 | 95 | 21 | 123 | 135 |

| df = 2 | | Odds ratio (OR): multiple model | | | | | |
|---|---|---|---|---|---|---|---|
| Chi_value | Chi_exact _p-Value | Risk allele | OR | CI | HWE cas_HW | HWE cas_HW | Sample call rate cas_call_rate | Sample call rate con_call_rate |
| 5.287 | 3.20E−02 | A1 A | 2.06 | (1.085, 3.9) | .174, HWE | .067, HWE | 0.99 | 1 |
| 6.041 | 4.88E−02 | A1 A | 1.37 | (1.055, 1.785) | .569, HWE | .127, HWE | 1 | 0.98 |
| 7.299 | 2.60E−02 | A2 C | 1.41 | (1.085, 1.812) | 1.584, HWE | 2.407, HWE | 0.92 | 0.99 |
| 6.155 | 4.61E−02 | A1 G | 1.36 | (1.044, 1.774) | .657, HWE | .419, HWE | 0.99 | 0.97 |
| 10.754 | 4.62E−03 | A2 G | 1.52 | (1.182, 1.961) | .195, HWE | .029, HWE | 0.87 | 0.94 |
| 27.984 | 8.38E−07 | A2 T | 1.49 | (1.156, 1.946) | 44.441, HWD | .075, HWE | 0.87 | 0.98 |
| 7.34 | 2.55E−02 | A2 G | 1.43 | (1.103, 1.832) | .945, HWE | .071, HWE | 0.9 | 0.98 |
| 14.733 | 6.32E−04 | A2 C | 1.52 | (1.164, 1.965) | 9.12, HWD | .185, HWE | 0.88 | 0.99 |
| 17.789 | 1.37E−04 | A1 G | 1.49 | (1.102, 2.012) | 56.139, HWD | 2.444, HWE | 0.9 | 0.97 |
| 6.166 | 4.58E−02 | A1 G | 1.30 | (1.016, 1.666) | 1.747, HWE | .287, HWE | 0.89 | 0.98 |
| 6.729 | 3.46E−02 | A2 A | 1.39 | (1.068, 1.792) | .535, HWE | .185, HWE | 0.95 | 0.99 |
| 7.056 | 2.94E−02 | A1 A | 1.39 | (1.071, 1.805)) | .083, HWE | .863, HWE | 0.92 | 0.94 |

TABLE 2

Characteristics of the polymorphic sequences of SEQ ID NOS: 1-12

| ASSAY_ID | rs | Chromosome # | Chromosome position | Band | Gene | Description | SNP function | Amino acid change |
|---|---|---|---|---|---|---|---|---|
| CCK048 | rs2863383 | 3 | 167396140 | 3q26.1 | Between genes | — | Between genes | No change |
| CCK061 | rs7151139 | 14 | 21933597 | 14q11.2 | C14orf120 | Chromosome 14 orf 120 | Intron | No change |
| CCK117 | rs724454 | 4 | 91421840 | 4q22.1 | Between genes | — | Between genes | No change |
| CCK162 | rs10142383 | 14 | 21932663 | 14q11.2 | C14orf120 | Chromosome 14 orf 120 | Intron | No change |
| CCY_041 | rs1402026 | 5 | 114159705 | 5q22.3 | Between genes | — | Between genes | No change |
| CCY_056 | rs1485217 | 3 | 3917830 | 3p26.2 | Between genes | — | Between genes | No change |
| CCY_065 | rs1996489 | 3 | 167399578 | 3q26.1 | Between genes | — | Between genes | No change |
| CCY_067 | rs2236261 | 14 | 21934642 | 14q11.2 | C14orf120 | Chromosome 14 orf 120 | coding-synon, reference | No change |
| CCY_071 | rs1340655 | 10 | 61325850 | 10q21.2 | ANK3 | ankyrin 3, node of Ranvier (ankyrin G) | Intron | No change |
| CCY_093 | rs1334856 | 13 | 82206386 | 13q31.1 | Between genes | — | Between genes | No change |
| CCY_202 | rs6573195 | 14 | 21934148 | 14q11.2 | C14orf120 | Chromosome 14 orf 120 | Intron | No change |
| CCY_205 | rs2295706 | 14 | 21935494 | 14q11.2 | C14orf120 | Chromosome 14 orf 120 | Intron | No change |

In Tables 1 and 2, the contents in columns are as defined below.

Assay_ID represents a marker name.

SNP is a polymorphic base of a SNP polymorphic site. Here, A1 and A2 represent a low mass allele and a high mass allele, respectively, as a result of sequence analysis according to a homogeneous MassEXTEND198 (hME) technique (SEQUENOM, Inc., San Diego, Calif.) and are optionally designated for convenience of experiments.

SNP sequence represents a sequence containing a SNP site, i.e., a sequence containing allele A1 or A2 at position 101.

At the allele frequency column, cas_A2, con_A2, and Delta respectively represent allele A2 frequency of a case group, allele A2 frequency of a normal group, and the absolute value of the difference between cas_A2 and con_A2. Here, cas_A2 is (genotype A2A2 frequency×2+genotype A1A2 frequency)/(the number of samples×2) in the case group and con_A2 is (genotype A2A2 frequency×2+genotype A1A2 frequency)/(the number of samples×2) in the normal group.

Genotype frequency represents the frequency of each genotype. Here, cas_A1A1, cas_A1A2, and cas_A2A2 are the number of persons with genotypes A1A1, A1A2, and A2A2, respectively, in the case group, and con_A1A1, con_A1A2, and con_A2A2 are the number of persons with genotypes A1A1, A1A2, and A2A2, respectively, in the normal group.

df=2 represents a chi-squared value with two degree of freedom. Chi-value represents a chi-squared value and p-value is determined based on the chi-value. Chi_exact_p-value represents p-value of Fisher's exact test of chi-square test. When the number of genotypes is less than 5, results of the chi-square test may be inaccurate. In this respect, determination of more accurate statistical significance (p-value) by the Fisher's exact test is required. The chi_exact_p-value is a variable used in the Fisher's exact test. In the present invention, when the p-value≦0.05, it is considered that the genotype of the case group is different from that of the normal group, i.e., there is a significant difference between the case group and the normal group.

At the risk allele column, when a reference allele is A2 and the allele A2 frequency of the case group is larger than the allele A2 frequency of the normal group (i.e., cas_A2>con_A2), the allele A2 is regarded as risk allele. In an opposite case, allele A1 is regarded as risk allele.

Odds ratio represents the ratio of the probability of risk allele in the case group to the probability of risk allele in the normal group. In the present invention, the Mantel-Haenszel odds ratio method was used. CI represents 95% confidence interval for the odds ratio and is represented by (lower limit of the confidence interval, upper limit of the confidence interval). When 1 falls under the confidence interval, it is considered that there is insignificant association of risk allele with disease.

HWE represents that the result satisfied Hardy-Weinberg Equilibrium. Here, con_HWE and cas_HWE represent degree of deviation from the Hardy-Weinberg Equilibrium in the normal group and the case group, respectively. Based on chi_value=6.63 (p-value=0.01, df=1) in a chi-square (df=1) test, a value larger than 6.63 was regarded as Hardy-Weinberg Disequilibrium (HWD) and a value smaller than 6.63 was regarded as Hardy-Weinberg Equilibrium (HWE).

Call rate represents the number of genotype-interpretable samples to the total number of samples used in experiments. Here, cas_call_rate and con_call_rate represent the ratio of the number of genotype-interpretable samples to the total number (300 persons) of samples used in the case group and the normal group, respectively.

rs represents SNP identification number in NCBI dbSNP.

Tables 1 and 2 present characteristics of SNP markers based on the NCBI build 119 (Feb. 1, 2005).

As shown in Tables 1 and 2, according to the chi-square test of the polymorphic markers of SEQ ID NOS: 1-12 of the present invention, chi_exact_p-value ranges from 0.0000008 to 0.049 in 95% confidence interval. This shows that there are significant differences between expected values and measured values in allele occurrence frequencies in the polymorphic markers of SEQ ID NOS: 1-12. Odds ratio ranges from 1.30 to 2.06, which shows that the polymorphic markers of SEQ ID NOS: 1-12 are associated with colorectal cancer.

Therefore, the polynucleotide according to the present invention can be efficiently used in diagnosis, fingerprinting analysis, or treatment of colorectal cancer. In detail, the polynucleotide of the present invention can be used as a primer or a probe for diagnosis of colorectal cancer. Furthermore, the polynucleotide of the present invention can be used as antisense DNA or a composition for treatment of colorectal cancer.

The present invention also provides an allele-specific polynucleotide for diagnosis of colorectal cancer, which is hybridized with a polynucleotide including at least 10 contiguous nucleotides containing the nucleotide of a polymorphic site of a nucleotide sequence selected from the group consisting of the nucleotide sequences of SEQ ID NOS: 1-12, or a complement thereof.

The allele-specific polynucleotide refers to a polynucleotide specifically hybridized with each allele. That is, the allele-specific polynucleotide has the ability that distinguishes nucleotides of polymorphic sites within the polymorphic sequences of SEQ ID NOS: 1-12 and specifically hybridizes with each of the nucleotides. The hybridization is performed under stringent conditions, for example, conditions of 1M or less in salt concentration and 25° C. or more in temperature. For example, conditions of 5×SSPE (750 mM NaCl, 50 mM Na Phosphate, 5 mM EDTA, pH 7.4) and 25-30° C. are suitable for allele-specific probe hybridization.

In the present invention, the allele-specific polynucleotide may be a primer. As used herein, the term "primer" refers to a single stranded oligonuleotide that acts as a starting point of template-directed DNA synthesis under appropriate conditions, for example in a buffer containing four different nucleoside triphosphates and polymerase such as DNA or RNA polymerase or reverse transcriptase and an appropriate temperature. The appropriate length of the primer may vary according to the purpose of use, generally 15 to 30 nucleotides. Generally, a shorter primer molecule requires a lower temperature to form a stable hybrid with a template. A primer sequence is not necessarily completely complementary with a template but must be complementary enough to hybridize with the template. Preferably, the 3' end of the primer is aligned with a nucleotide (n) of each polymorphic site of SEQ ID NOS: 1-12. The primer is hybridized with a target DNA containing a polymorphic site and starts an allelic amplification in which the primer exhibits complete homology with the target DNA. The primer is used in pair with a second primer hybridizing with an opposite strand. Amplified products are obtained by amplification using the two primers, which means that there is a specific allelic form. The primer of the present invention includes a polynucleotide fragment used in a ligase chain reaction (LCR).

In the present invention, the allele-specific polynucleotide may be a probe. As used herein, the term "probe" refers to a hybridization probe, that is, an oligonucleotide capable of sequence-specifically binding with a complementary strand of a nucleic acid.

Such a probe may be a peptide nucleic acid as disclosed in Science 254, 1497-1500 (1991) by Nielsen et al. The probe according to the present invention is an allele-specific probe. In this regard, when there are polymorphic sites in nucleic acid fragments derived from two members of the same species, the probe is hybridized with DNA fragments derived from one member but is not hybridized with DNA fragments derived from the other member. In this case, hybridization conditions should be stringent enough to allow hybridization with only one allele by significant difference in hybridization strength between alleles. Preferably, the central portion of the probe, that is, position 7 for a 15 nucleotide probe, or position 8 or 9 for a 16 nucleotide probe, is aligned with each polymorphic site of the nucleotide sequences of SEQ ID NOS: 1-12. Therefore, there may be caused a significant difference in hybridization between alleles. The probe of the present invention can be used in diagnostic methods for detecting alleles. The diagnostic methods include nucleic acid hybridization-based detection methods, e.g., southern blot. In a case where DNA chips are used for the nucleic acid hybridization-based detection methods, the probe may be provided as an immobilized form on a substrate of a DNA chip.

The present invention also provides a microarray for diagnosis of colorectal cancer, including the polynucleotide according to the present invention or the complementary polynucleotide thereof. The polynucleotide of the microarray may be DNA or RNA. The microarray is the same as a common microarray except that it includes the polynucleotide of the present invention.

The present invention also provides a colorectal cancer diagnostic kit including the polynucleotide of the present invention. The colorectal cancer diagnostic kit may include reagents necessary for polymerization, e.g., dNTPs, various polymerases, and a colorant, in addition to the polynucleotide according to the present invention.

The present invention also provides a method of diagnosing colorectal cancer in an individual, which includes: isolating a nucleic acid sample from the individual; and determining a nucleotide (n) of at least one polymorphic site (position 101) within polynucleotides of SEQ ID NOS: 1-12 or complementary polynucleotides thereof. Here, when the nucleotide of the at least one polymorphic site of the sample nucleic acid is the same as at least one risk allele presented in Tables 1 and 2, it is determined that the individual has a higher likelihood of being diagnosed as at risk of developing colorectal cancer.

The operation of isolating the nucleic acid sample from the individual may be carried out by a common DNA isolation method. For example, the nucleic acid sample can be obtained by amplifying a target nucleic acid by polymerase chain reaction (PCR) followed by purification. In addition to PCR, there may be used LCR (Wu and Wallace, Genomics 4, 560 (1989), Landegren et al., Science 241, 1077 (1988)), transcription amplification (Kwoh et al., Proc. Natl. Acad. Sci. USA 86, 1173 (1989)), self-sustained sequence replication (Guatelli et al., Proc. Natl. Acad. Sci. USA 87, 1874 (1990)), or nucleic acid sequence based amplification (NASBA). The last two methods are related with isothermal reaction based on isothermal transcription and produce 30 or 100-fold RNA single strands and DNA double strands as amplification products.

According to an embodiment of the present invention, the operation of determining the nucleotide (n) of the at least one polymorphic site includes hybridizing the nucleic acid sample onto a microarray on which polynucleotides for diagnosis or treatment of colorectal cancer, including at least 10 contiguous nucleotides derived from the group consisting of nucleotide sequences of SEQ ID NOS: 1-12 and including a nucleotide of a polymorphic site (position 101), or complementary polynucleotides thereof are immobilized; and detecting the hybridization result.

A microarray and a method of preparing a microarray by immobilizing a probe polynucleotide on a substrate are well known in the pertinent art. Immobilization of a probe polynucleotide associated with colorectal cancer of the present invention on a substrate can be easily performed using a conventional technique. Hybridization of nucleic acids on a microarray and detection of the hybridization result are also well known in the pertinent art. For example, the detection of the hybridization result can be performed by labeling a nucleic acid sample with a labeling material generating a detectable signal, such as a fluorescent material (e.g., Cy3 and Cy5), hybridizing the labeled nucleic acid sample onto a microarray, and detecting a signal generated from the labeling material.

Hereinafter, the present invention will be described more specifically by Examples. However, the following Examples are provided only for illustrations and thus the present invention is not limited to or by them.

EXAMPLES

Example 1

In this Example, DNA samples were extracted from blood streams of a patient group consisting of 300 Korean men and women that had been diagnosed as colorectal cancer patients and had been being under treatment and a normal group consisting of 300 Korean men and women free from symptoms of colorectal cancer patient group, and occurrence frequencies of specific SNPs were evaluated. The SNPs were selected from a known database NCBI dbSNP (Single Nucleotide Polymorphism Database) or SEQUENOM RealSNP™ Assay Database. Primers hybridizing with sequences around the selected SNPs were used to assay nucleotides of SNPs in the DNA samples.

1. Preparation of DNA Samples

DNA samples were extracted from blood streams of colorectal cancer patients and normal persons. DNA extraction was performed according to a known extraction method (Molecular cloning: A Laboratory Manual, p 392, Sambrook, Fritsch and Maniatis, 2nd edition, Cold Spring Harbor Press, 1989) and the specification of a commercial kit manufactured by Centra system. Among extracted DNA samples, only DNA samples having a purity (measured by $A_{260}/A_{280}$ nm ratio) of at least 1.6 were used.

2. Amplification of Target DNAs

Target DNAs, which are predetermined DNA regions containing SNPs to be analyzed, were amplified by PCR. The PCR was performed by a common method as the following conditions. First, target genomic DNAs were diluted to concentration 2.5 ng/ml. Then, the following PCR mixture was prepared.

| | |
|---|---|
| Water (HPLC grade) | 2.24 μl |
| 10× buffer (15 mM MgCl$_2$, 25 mM MgCl$_2$) | 0.5 μl |
| dNTP Mix (GIBCO) (25 mM for each) | 0.04 μl |
| Taq pol (HotStar) (5 U/μl) | 0.02 μl |
| Forward/reverse primer Mix (1 μM for each) | 0.02 μl |
| DNA | 1.00 μl |
| Total volume | 5.00 μl |

Here, the forward and reverse primers were designed based on upstream and downstream sequences of SNPs in known database. These primers are listed in Table 3 below.

The condition of PCR were as follows: incubation at 95° C. for 15 minutes; denaturation at 95° C. for 30 seconds, annealing at 56° C. for 30 seconds, and extension at 72° C. for 1 minute and these are repeated 45 times; and finally incubation at 72° C. for 3 minutes and storage at 4° C. As a result, amplified target DNA fragments which were 200 or less nucleotides in length were obtained.

3. Analysis of Nucleotides of SNPs in Amplified Target DNA Fragments

Analysis of the nucleotides of SNPs in the amplified target DNA fragments was performed using a homogeneous MassLXTLND™ (hME) technique available from SEQUENOM, Inc., San Diego, Calif. The principle of the MassLXTLND™ technique is as follows. First, primers (also called as "extension primers") ending immediately one base before SNPs within the target DNA fragments were designed. Then, the primers were hybridized with the target DNA fragments and DNA polymerization was initiated. At this time, a polymerization solution contained a reagent (e.g., ddTTP) terminating the polymerization immediately after the incorporation of a nucleotide complementary to a first allelic nucleotide (e.g., A allele). In this regard, when the first allele (e.g., A allele) exists in the target DNA fragments, products in which only a nucleotide (e.g., T nucleotide) complementary to the first allele extended from the primers will be obtained. On the other hand, when a second allele (e.g., G allele) exists in the target DNA fragments, a nucleotide (e.g., C nucleotide) complementary to the second allele is added to the 3'-ends of the primers and then the primers are extended until a nucleotide complementary to the closest first allele nucleotide (e.g., T nucleotide) is added. The lengths of products extended from the primers were determined by mass spectrometry. Therefore, alleles present in the target DNA fragments could be identified. Illustrative experimental conditions were as follows.

First, unreacted dNTPs were removed from the PCR products. For this, 1.53 μl of pure water, 0.17 μl of HME buffer, 0.30 μl of shrimp alkaline phosphatase (SAP) were added and mixed in. 1.5 ml tubes to prepare SAP enzyme solutions. The tubes were centrifuged at 5,000 rpm for 10 seconds. Thereafter, the PCR products were added to the SAP solution tubes, sealed, incubated at 37° C. for 20 minutes and then 85° C. for 5 minutes, and stored at 4° C.

Next, homogeneous extension was performed using the target DNA fragments as templates. The compositions of reaction solutions for the extension were as follows.

| | |
|---|---|
| Water (nanoscale pure water) | 1.728 μl |
| hME extension mix (10× buffer containing 2.25 mM d/ddNTPs) | 0.200 μl |
| Extension primers (100 μM for each) | 0.054 μl |
| Thermosequenase (32 U/μl) | 0.018 μl |
| Total volume | 2.00 μl |

The reaction solutions were thoroughly mixed with the previously prepared target DNA solutions and subjected to spin-down centrifugation. Tubes or plates containing the resultant mixtures were compactly sealed and incubated at 94° C. for 2 minutes, followed by 40 cycles at 94° C. for 5 seconds, at 52° C. for 5 seconds, and at 72° C. for 5 seconds, and storage at 4° C. The homogeneous extension products thus obtained were washed with a resin (SpectroCLEAN). Extension primers used in the extension are listed in Table 3 below.

TABLE 3

Primers for amplification and extension primers for homogeneous extension for target DNAs

| Marker | Amplification primer (SEQ ID NO.) | | Extension primer (SEQ ID NO.) |
| --- | --- | --- | --- |
| | Forward primer | Reverse primer | |
| CCK048 | 13 | 14 | 15 |
| CCK061 | 16 | 17 | 18 |
| CCK117 | 19 | 20 | 21 |
| CCK162 | 22 | 23 | 24 |
| CCY_041 | 25 | 26 | 27 |
| CCY_056 | 28 | 29 | 30 |
| CCY_065 | 31 | 32 | 33 |
| CCY_067 | 34 | 35 | 36 |
| CCY_071 | 37 | 38 | 39 |
| CCY_093 | 40 | 41 | 42 |
| CCY_202 | 43 | 44 | 45 |
| CCY_205 | 46 | 47 | 48 |

Nucleotides of polymorphic sites in the extension products were assayed using mass spectrometry, MALDI-TOF (Matrix Assisted Laser Desorption and Ionization-Time of Flight). The MALDI-TOF is operated according to the following principle. When an analyte is exposed to a laser beam, it flies toward a detector positioned at the opposite side in a vacuum state, together with an ionized matrix (3-hydroxypicolinic acid). At this time, the time taken for the analyte to reach the detector is calculated. A material with a smaller mass reaches the detector more rapidly. The nucleotides of SNPs in the target DNA fragments are determined based on a difference in mass between the DNA fragments and known nucleotide sequences of the SNPs.

Determination results of nucleotides of polymorphic sites of the target DNAs using the MALDI-TOF are shown in Tables 1 and 2 above. Each allele may exist in the form of homozygote or heterozygote in an individual. According to Mendel's Law of inheritance and Hardy-Weinberg Law, a genetic makeup of alleles constituting a population is maintained at a constant frequency. When the genetic makeup is statistically significant, it can be considered to be biologically meaningful. The SNPs according to the present invention occur in colorectal cancer patients at a statistically significant level, as shown in Tables 1 and 2, and thus, can be efficiently used in diagnosis of colorectal cancer.

The polynucelotide according to the present invention can be used for diagnosis, treatment, or fingerprinting analysis of colorectal cancer.

The microarray and diagnostic kit including the polynucleotide according to the present invention can be used for efficient diagnosis of colorectal cancer.

The method of analyzing polynucleotides associated with colorectal cancer according to the present invention can efficiently detect the presence or a risk of colorectal cancer.

What is claimed is:

1. A method of determining an increased risk of developing colorectal cancer in a human, which comprises:

determining in a nucleic acid sample from a human the nucleotide base at a polymorphic site at position 101 of SEQ ID NO: 5, and determining risk of developing colorectal cancer in the human, wherein determining the base is guanine (G) indicates an increased risk of developing colorectal cancer compared to determining the base is thymine (T).

2. The method of claim 1, wherein the operation of determining the nucleotide base of the polymorphic site comprises:

hybridizing the nucleic acid sample onto a microarray on which is immobilized a polynucleotide comprising
  (a) at least 10 contiguous nucleotides of SEQ ID NO: 5 comprising position 101, or
  (b) the complement of(a); and
detecting a hybridization result.

3. The method of claim 1, further comprising determining a genotype in the nucleic acid sample at the polymorphic site, and wherein determining that the genotype is GT or GG indicates increased risk of developing colorectal cancer compared to determining the genotype is TT.

* * * * *